(12) United States Patent
Garrison et al.

(10) Patent No.: US 8,211,160 B2
(45) Date of Patent: *Jul. 3, 2012

(54) STENT GRAFT ASSEMBLY AND METHOD

(75) Inventors: Michi E. Garrison, Half Moon Bay, CA (US); Leon V. Rudakov, Belmont, CA (US)

(73) Assignee: Nfocus Neuromedical, Inc., Palo Alto, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 12/028,742

(22) Filed: Feb. 8, 2008

(65) Prior Publication Data

US 2008/0125852 A1    May 29, 2008

Related U.S. Application Data

(63) Continuation of application No. 10/255,199, filed on Sep. 26, 2002, now abandoned, which is a continuation-in-part of application No. 09/560,427, filed on Apr. 28, 2000, now Pat. No. 6,520,984.

(51) Int. Cl.
*A61F 2/06* (2006.01)
*A61F 11/00* (2006.01)

(52) U.S. Cl. .............. 623/1.13; 623/1.11; 623/1.12; 623/1.23; 623/1.25

(58) Field of Classification Search .......... 623/1.11, 623/1.12, 1.13, 1.14, 1.15, 1.16, 1.17, 1.18, 623/1.19, 1.2, 1.21; 606/108, 191, 195
See application file for complete search history.

(56) References Cited

U.S. PATENT DOCUMENTS

| | | | | | |
|---|---|---|---|---|---|
| 5,123,917 | A | * | 6/1992 | Lee | 623/22.26 |
| 5,776,141 | A | * | 7/1998 | Klein et al. | 623/1.11 |
| 5,824,037 | A | * | 10/1998 | Fogarty et al. | 623/1.13 |
| 6,231,598 | B1 | * | 5/2001 | Berry et al. | 623/1.15 |

* cited by examiner

*Primary Examiner* — Vy Q Bui

(74) *Attorney, Agent, or Firm* — Dickstein Shapiro LLP; Mark A. Stirrat

(57) ABSTRACT

A method for assembling a stent graft onto a balloon delivery catheter is disclosed. The method includes the steps of: assembling a graft over a stent with attached security rings and inserting the ends of the graft between the stent and the rings; placing the assembled stent graft on the delivery balloon of the delivery catheter; and crimping the stent graft onto the balloon. The stent may include a plurality of axially aligned belts that include a plurality of mid belts, and first and second end belts, where each of the mid belts includes a plurality of circumferentially spaced struts having first and second ends adjoining first sinusoidal-shaped elements, and each of the first and second end belts includes at least about twice the number of circumferentially spaced struts adjoining second sinusoidal-shaped elements. Also disclosed is a stent graft for use in practicing the method.

17 Claims, 3 Drawing Sheets

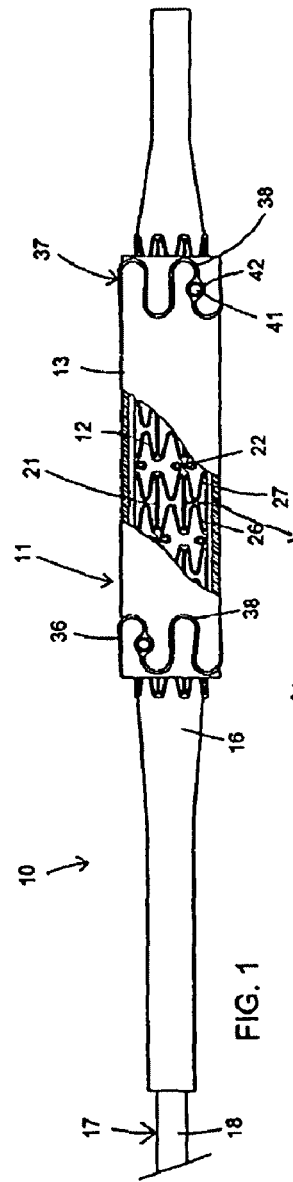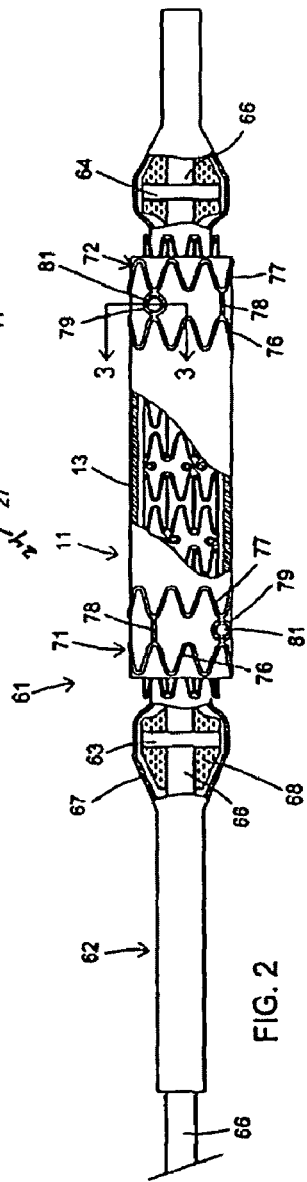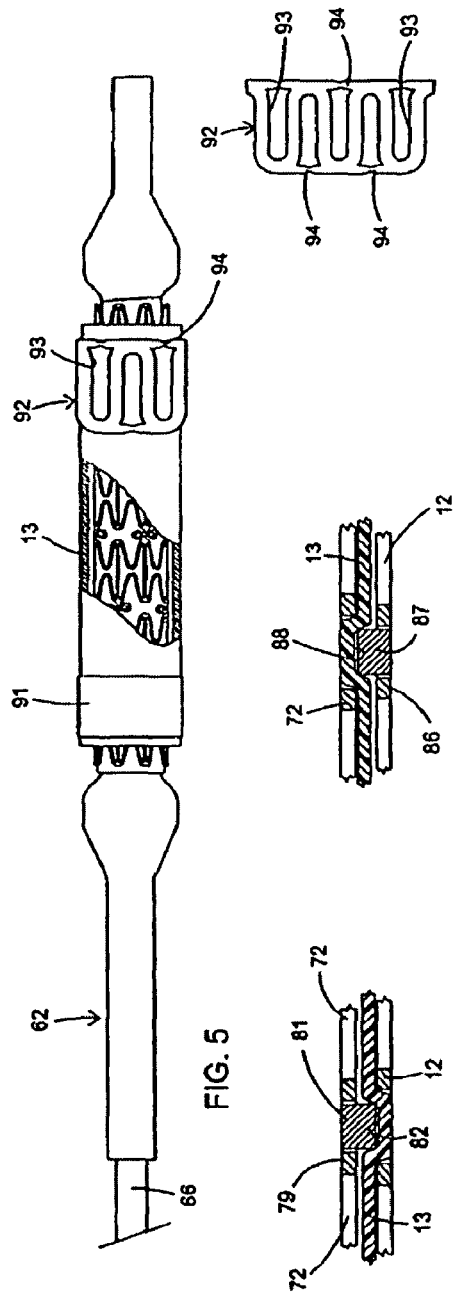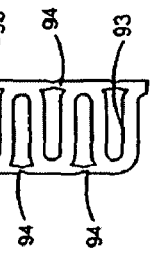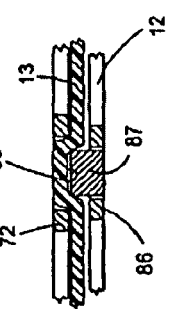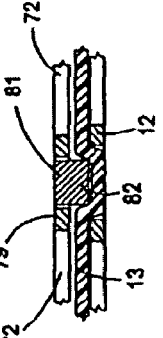

STENT GRAFT ASSEMBLY AND METHOD

CROSS REFERENCE TO RELATED APPLICATIONS

This application is a continuation of co-pending U.S. application Ser. No. 10/255,199 filed Sep. 26, 2002 which is a continuation-in-part of U.S. application Ser. No. 09/560,427 filed Apr. 28, 2000 and issued as U.S. Pat. No. 6,520,984 on Feb. 18, 2003 (abandoned), both of which are incorporated by reference herein in their entirety.

FIELD OF THE INVENTION

The present invention relates to a stent graft assembly and method, and more particularly to a stent graft assembly which includes security rings.

BACKGROUND OF THE INVENTION

A composite expandable device with polymeric covering and bioactive coating thereon, delivery apparatus and method are disclosed in U.S. Pat. No. 6,371,980, issued Apr. 16, 2002. In connection with the expandable stent and the polymeric covering forming a graft carried thereby it has been found that it may be possible for the graft to move or become dislodged from its most desirable position on the stent. There is therefore a need for a new and improved stent graft assembly and method which overcomes this possible difficulty.

SUMMARY OF THE INVENTION

In one aspect, the invention includes a stent graft that includes a stent and a graft in the form of a polymeric sleeve extending over at least a portion of the stent. Security rings are attached on opposite ends of the stent graft to prevent inadvertent displacement of the graft with respect to the stent during deployment of the stent graft into a vessel in a patient. In another embodiment, the security rings can readily accommodate expansion of the stent graft. One or both of the security rings may be attached to the stent with a weld. Preferably, the weld is a laser weld.

In one embodiment, the stent includes a plurality of axially aligned belts which include a plurality of mid belts, and first and second end belts. Each of the mid belts includes a plurality of circumferentially spaced struts having first and second ends adjoining first sinusoidal-shaped elements. Each of said first and second end belts includes at least about twice the number of circumferentially spaced struts adjoining second sinusoidal-shaped elements compared to the number of the struts in the mid belts.

In another embodiment, the first and second sinusoidal-shaped elements have hinge points, and the second sinusoidal-shaped elements have narrower hinge points relative to the hinge points of the first sinusoidal-shaped elements.

The graft may be formed of ePTFE. In one embodiment of the invention, the graft includes a bioactive coating that is disposed on the graft.

One or more of the security rings of the invention may include a radiopaque marker carried thereon. In one embodiment, one or both of the security rings includes an eyelet and the radiopaque material is disposed in the eyelet.

Another aspect of the invention includes a method for assembling a stent graft onto a balloon delivery catheter. The method includes the steps of: assembling a graft over a stent with attached security rings and inserting the ends of the graft between the stent and the rings; placing the assembled stent graft on the delivery balloon of the delivery catheter; and crimping the stent graft onto the balloon. One or both of the security rings may be attached to the stent with a weld. Preferably, the weld is a laser weld.

In one embodiment of the method of the invention, the stent includes a plurality of axially aligned belts which include a plurality of mid belts, and first and second end belts. Each of the mid belts includes a plurality of circumferentially spaced struts having first and second ends adjoining first sinusoidal-shaped elements. Each of said first and second end belts includes at least about twice the number of circumferentially spaced struts adjoining second sinusoidal-shaped elements compared to the number of the struts in the mid belts.

In another embodiment, the first and second sinusoidal-shaped elements have hinge points, and the second sinusoidal-shaped elements have narrower hinge points relative to the hinge points of the first sinusoidal-shaped elements.

The graft may be formed of ePTFE. In one embodiment of the invention, the graft includes a bioactive coating that is disposed on the graft.

One or more of the security rings of the invention may includes a radiopaque marker carried thereon. In one embodiment, one or both of the security rings includes an eyelet and the radiopaque material is disposed in the eyelet.

Additional objects and features of the invention will appear from the following description in which the preferred embodiments are set forth in detail in conjunction with the accompanying drawings.

BRIEF DESCRIPTION OF THE DRAWINGS

FIG. 1 is a side elevational view of a stent graft assembly incorporating the present invention mounted on the distal extremity of a balloon delivery catheter;

FIG. 2 is a side elevational view of another embodiment of a stent graft assembly incorporating the present invention also mounted on the distal extremity of a balloon delivery catheter;

FIG. 3 is a cross-sectional view taken along the line 3-3 of FIG. 2;

FIG. 4 is a view similar to FIG. 3 showing an alternate embodiment;

FIG. 5 is a side elevational view of a stent graft assembly with a certain portion of the stent graft being removed and showing the use of different types of security rings;

FIG. 6 is an enlarged view of one of the security rings shown in FIG. 5;

DETAILED DESCRIPTION OF THE INVENTION

Figure 7:
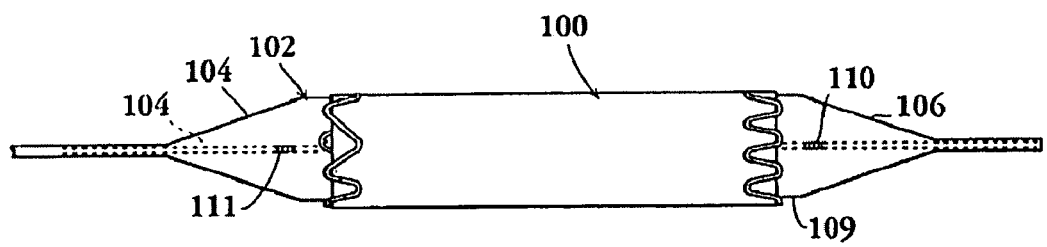
FIG. 7 is a view of a balloon with the stent graft with security rings mounted thereon according to one embodiment of the invention.

In general, the stent graft assembly incorporating the present invention is for use in placing a stent graft in a vessel of a patient and comprises a balloon delivery catheter having a distal extremity and having an inflatable balloon on the distal extremity. A stent graft is disposed over the inflatable balloon and is comprised of a stent and an outer polymeric sleeve, the sleeve having first and second ends. First and second expandable security rings are disposed over the first and second ends of the graft and serve to secure the first and second ends of the graft to the stent to prevent inadvertent displacement of the sleeve with respect to the stent during deployment of the stent graft into the vessel of the patient.

More particularly as shown in FIG. 1 of the drawings, the stent graft assembly includes a stent graft 11 which consists of a stent 12 which is covered by a polymeric sleeve 13. As shown in FIG. 1, the stent graft 11 is disposed over an inflatable balloon 16 on the distal extremity of a balloon delivery catheter 17 of a conventional type and forming a part of the assembly 10. The balloon delivery catheter 17 includes a multi-lumen shaft 18 which incorporates a balloon inflation lumen (not shown) and may incorporate a guide wire lumen (not shown).

The balloon delivery catheter 17 and the stent graft 11 consisting of stent 12 and the polymeric sleeve 13 are disclosed in U.S. Pat. No. 6,371,980, issued Apr. 16, 2002, which is incorporated by reference herein in its entirety, and therefore will not be described in detail. As disclosed therein, the stent 12 is in the form of an expandable frame and consists of a plurality of axially spaced-apart circular belts 21 which are interconnected by sinusoidal interconnector 22. Each belt 21 is comprised of a plurality of circumferentially spaced-apart elongate struts 24. Sinusoidal-shaped elements 26 and 27 adjoin the ends of the struts 24 and form in conjunction therewith the circular belts 21. The sinusoidal-shaped interconnectors 22 provided for interconnecting the belts 21 are at circumferentially spaced-apart positions to provide a stent 12 which when expanded is capable of providing circumferential support while at the same time being axially flexible.

The stent 12 is typically formed of a suitable metal such as stainless steel, titanium and other metals and alloys thereof. It is desirable that the material utilized for the frame be biocompatible with the fluids and tissue of the human body.

The sleeve 13 is in the form of a tubular member of a size so that it can slip over the stent 12 when it is in an unexpanded condition and preferably has a length so that the extreme ends of the stent 12 extend beyond the sleeve as shown in FIG. 1. The sleeve 13 is typically formed of a polymeric material such as ePTFE.

In order to ensure that the polymeric sleeve 13 remains in the desired position on the stent 12, security rings 36 and 37 have been positioned over the outer ends of the sleeve 13. The security rings 36 and 37 typically can be formed of a metal and preferably the same metal which is used for the stent 12, for example, stainless steel or titanium or alloys thereof. The rings 36 and 37 have sinusoidal-shaped convolutions 38 so that they can be expanded with the stent graft when the stent graft is expanded as hereinafter described. By way of example, the security rings can be formed from laser cut tubing in the same manner as stents having a suitable wall thickness of 0.003" to 0.006". The inner surfaces of the security rings can be left unpolished so that they have a rougher inner surface finish to enhance gripping to the outer surface of the sleeve 13. Alternatively, a texture can be applied to the inner surface to enhance the gripping capabilities of the security ring.

Figure 8:
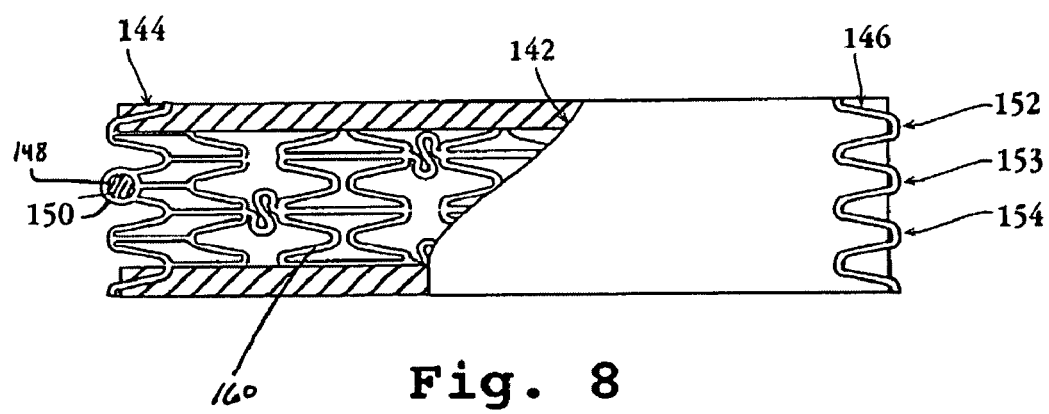
FIG. 8 is a detailed view of the stent graft with security rings.
Figure 9:
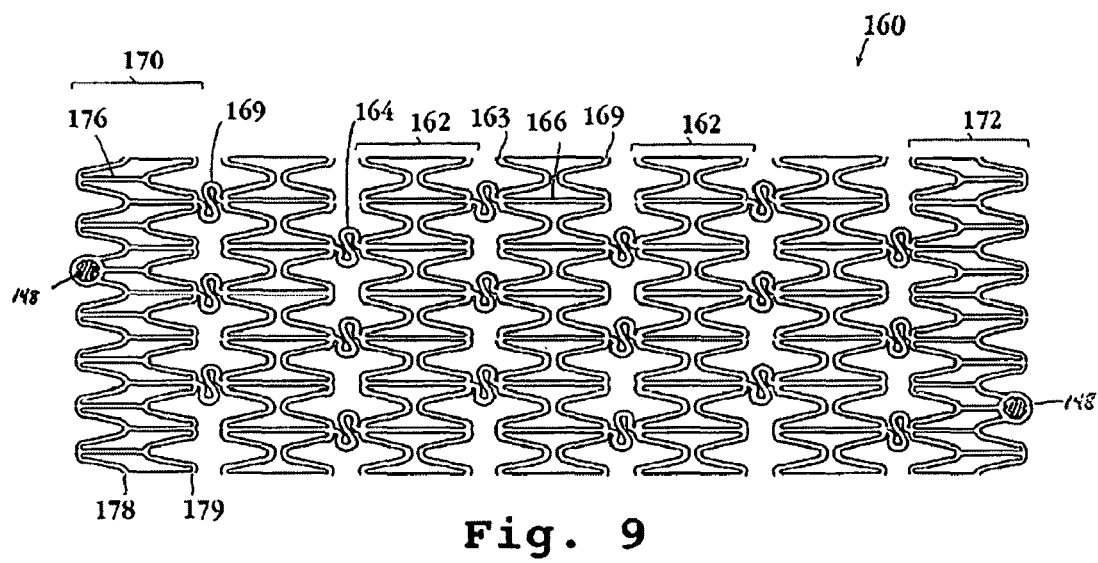
FIG. 9 is a plan view of a stent which has been split apart longitudinally and spread out to show its construction.

A radiopaque marker 41 is carried by at least one and, if desired, both of the security rings 36 and 37, as in FIGS. 1 and 2. Thus, as shown, a radiopaque marker 41 is provided on the security ring 37 and can be of a suitable radiopaque material such as gold which has been cold worked or forged into an eyelet receptacle 42 formed as a part of the convolutions 38. Alternately, as shown in FIGS. 8 and 9, the radiopaque marker 148 is provided on either or both ends of the stent 140 in a similar eyelet receptacle 150.

In use of the stent graft assembly 10 and the stent graft 11 of the present invention with the method of the present invention, the stent 12 can be placed upon a support mandrel (not shown) after which the sleeve 13 is slipped onto the stent to provide the stent graft 11. The stent graft 11 is then placed on the balloon 16 of the balloon delivery catheter 17. The stent graft 11 is then crimped onto the balloon 16 with a crimping tool (not shown). The security rings 36 and 37 are then placed over the sleeve 13 and crimped onto the ends of the sleeve 13 by a crimping tool to ensure that the security rings 36 and 37 remain in place on the ends of the sleeve 13 and also to ensure that the ends of the graft 11 frictionally engage the stent 12 to retain the sleeve 13 in the desired position on the stent 12. Alternatively, the security rings 36 and 37 and the stent graft 11 can be crimped simultaneously.

The stent graft assembly 10 shown in FIG. 1 can now be utilized for positioning the stent graft 11 in a vessel of a patient in a conventional manner as for example by introducing the same through a femoral artery. The advancement of the stent graft 11 can be ascertained by observing the positioning of the radiopaque marker 41 and also by any radiopaque markers on the stent 12 and the balloon catheter 17. During advancement of the stent graft to the desired site, the security rings 36 and 37 serve to ensure that the sleeve 13 will not accidentally become dislodged or shifted in position on the stent 12. After the stent graft has been delivered to the desired position in the vessel of the patient, the balloon 16 of the balloon delivery catheter 17 can be expanded to expand the stent 12 and the sleeve 13 carried thereby as well as the security rings 36 and 37.

After the stent graft 11 has been delivered and then expanded the desired amount, the balloon 16 of the balloon delivery catheter 17 can be deflated and the balloon delivery catheter 17 removed in a conventional manner. The stent graft 11 will remain in place. Its position can be ascertained by observing the position of the radiopaque marker 41.

Another embodiment of a stent graft assembly incorporating the present invention is shown in the stent graft assembly 61 in FIG. 2. The balloon delivery catheter 62 shown therein shows the use of radiopaque marker bands 63 and 64 positioned on a shaft 66 on opposite ends of the balloon 67 and held in place by suitable means such as an epoxy 68 and disposed on opposite ends of the stent graft 11 and serve as enlargements to prevent the inadvertent dislodgement of the stent and/or the graft from the balloon during deployment of the stent graft 11.

In addition, as in the previous embodiments, security rings 71 and 72 are provided on opposite ends of the stent 12 and the sleeve 13. Security rings 71 and 72 are each comprised of two elongate elements 76 and 77 in the forms of waves or convolutions which are sinusoidal in shape and which are joined together by circumferentially spaced-apart axially extending struts 78 and eyelets 79. As with the security rings 36 and 37, it can be seen that the security rings 71 and 72 can be readily crimped into place and expanded in the same manner as the security rings 36 and 37. The eyelets 79 carry radiopaque markers 81. As with the security rings 36 and 37 the inner surfaces of the elements 76 and 77 can be left unpolished or with a textured surface for frictionally engaging the outer surface of the polymeric sleeve 13.

In order to further enhance the engagement between the polymeric sleeve 13 on the stent 12, the radiopaque marker 81 as shown in FIG. 3 can protrude out of the eyelet 79 so that it can form an indentation 82 with the sleeve 13 which extends into an open space in the stent 12 to further ensure a good engagement between the sleeve 13 and the stent 12 to prevent dislodgement of the sleeve 13 and ring 71 or 72 from the stent 12. In a similar manner as shown in FIG. 4, an eyelet 86 provided on the stent 12 may also carry a radiopaque marker 87 protruding radially and forming an indentation 88 in the inner surface of the sleeve 13 and to extend into a space in the security ring 72 to further ensure good engagement between the sleeve 13 and the stent 12.

Operation and use of the stent graft assembly 61 shown in FIG. 2 is very similar to that hereinbefore described with respect to FIG. 1 with the principal difference being that the security rings 71 and 72 have enhanced friction engaging capabilities over the security rings 36 and 37 shown in FIG. 1. In addition, the balloon delivery catheter 62, by providing the marker bands 63 and 64 on opposite extremities of the stent graft 11 also ensure that the stent graft 11 cannot accidentally become dislodged during deployment of the stent graft 11.

Still another embodiment of a stent graft assembly incorporating the present invention is shown in FIG. 5 in which the balloon delivery catheter 62 as shown therein is similar to the one hereinbefore described. The stent graft 11 is also similar to those hereinbefore described. However, in FIG. 5 there is shown the use of security rings 91 or 92 (showing two different designs) mounted on opposite ends of the sleeve 13. The security ring 91 is in the form of a stretchable polymer which can be stretched and fitted over one end of the sleeve 13 to frictionally retain the security ring 91 on the sleeve 13 and similarly to retain the sleeve 13 on the stent 12. Alternatively, as shown with the security ring 92, a less stretchable band of polymeric material can be utilized which is provided with circumferentially spaced-apart cutouts 93 therein which as shown in detail in FIG. 6 are positioned in such a manner so as to provide weakened regions 94 associated with each of the cutouts 93 but being staggered or provided on opposite sides of the security ring 92 so that when the stent graft 11 is expanded, these weakened regions will or can break apart to provide a zig-zag shape or a substantially sinusoidal wave-like shape for the expanded security ring 92. Thus, it can be seen that a polymeric security ring can be provided which firmly secures the graft to the stent while still permitting expansion of the stent and graft after the stent graft assembly 11 has been deployed to the desired position.

As shown in FIG. 7, the stent graft 100 is shown mounted on a delivery apparatus 102. The apparatus 102 is provided with a central lumen 103 which is adapted to receive a conventional guide wire. The lumen 103 extends through the apparatus 102 and an opening (not shown) is provided in the apparatus for expanding the apparatus. The apparatus 102 has a substantially continuous diameter and is provided with distal and proximal portions 104 and 106 and an intermediate portion 107 which serves as a working portion of the apparatus, having a length which will accept the length of the stent graft 100. Radiopaque marker bands 110 and 111 are provided on the portion of the central lumen 103 extending through the apparatus and are mounted in the distal and proximal portions 104 and 106 as shown adjacent to the intermediate portion 102.

Figure 10:
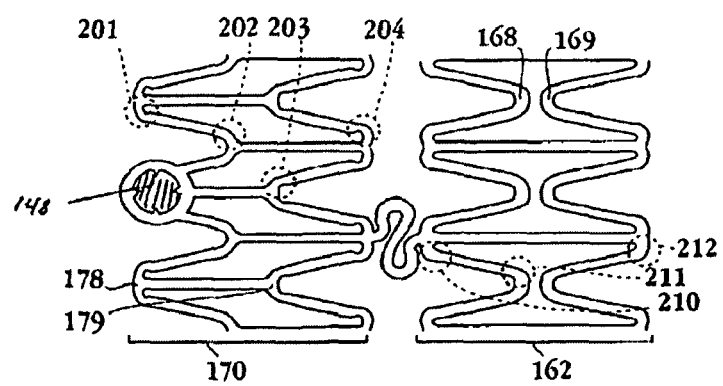
FIG. 10 is an enlarged view of a portion of the stent shown in FIG. 9.

As illustrated in FIG. 10, the stent 160 includes a plurality of serially-connected belts 162 which are axially aligned with each other and are interconnected by sinusoidal interconnector 164. Each belt 162 includes a plurality of circumferentially spaced-apart elongate struts 166. Sinusoidal-shaped elements 168 and 169 adjoin the ends of the struts 166 and form in conjunction therewith the circular belts 162. The sinusoidal-shaped interconnectors 164 provided for interconnecting the belts 162 are at circumferentially spaced-apart positions to provide a stent 160. Stent 160 is capable of providing circumferential support while, at the same time, being axially flexible. The stent may be formed by forming the desired pattern directly out of a tube, e.g. by laser cutting or chemical etching. Alternatively, the desired pattern may be formed out of a flat sheet, e.g. by laser cutting or chemical etching, and then rolling that flat sheet into a tube and joining the edges, e.g. by welding. Any other suitable manufacturing method known in the art may be employed for manufacturing a stent in accordance with the invention. Furthermore, stents may be formed by etching a pattern into a material or mold and depositing stent material in the pattern, such as by chemical vapor deposition or the like. Such stents may be formed of plastic, metal or other materials and may exhibit a multitude of configurations. The metals from which such stents are formed may include stainless steels, titanium, Nitinol, and tantalum among others.

In one embodiment, stent 160 includes serially-connected belts 162, and two end belts 170 and 172. All belts are connected with serpentine interconnectors 164. Each end belt 170 and 172 includes a plurality of circumferentially spaced-apart elongate struts 176. Belts 162 also include spaced-apart elongate struts 166. Serpentine interconnecting elements 164 are provided for interconnecting the plurality of belts 162 and the end belts 170 and 172 so that the belts 162 and end belts 170 and 172 extend along an axis while permitting axial bending between the belts 162 and the end belts 170 and 172. Thus, with the construction shown in FIG. 10 there are provided five belts 162 and two end portions 170 and 172 with six sets of interconnecting elements 164. The number of belts and interconnecting elements may vary depending on the desired length of the stent graft.

As described above, a polymer sleeve 142 extends over substantially the entire length of the stent 160. With reference to FIG. 10, there are twice as many struts 176 in end belts 170 and 172 as there are struts 166 in belts 162. The larger number of struts 176 in end belts 170 and 172 provides more circumferential support for the ends of the polymer sleeve (not shown), without causing unduly high radial strength at the ends of the stent graft. This has the advantage of preventing prolapse of the sleeve into the lumen of the stent graft due to blood flow after the stent graft is implanted into the vessel.

In addition, security rings 144 and 146 are provided on opposite ends of the stent 160 and the sleeve 142. The security rings 144 and 146 typically can be formed of a metal and preferably the same metal which is used for the stent 160, as for example stainless steel or titanium or alloys thereof. The security rings 144 and 146 have sinusoidal-shaped convolutions so that they can be expanded with the stent graft when the stent graft is expanded. A radiopaque marker 148 may be carried by at least one, and if desired both, of the security rings 144 and 146. Alternatively, as shown in FIG. 9, a radiopaque marker 148 is provided on both ends of the stent 160 and is of a suitable radiopaque material which has been cold worked, forged into, or deposited on an eyelet receptacle 150 formed as a part of the convolutions. Examples of materials which can be employed as radiopaque materials include, but are not limited to, iodine and its salts or compounds, barium and its salts or compounds, tungsten, rhenium, osmium, noble metals, palladium, gold, colloidal gold, silver, platinum, tantalum, iridium or their alloys. Preferably, the radiopaque material is gold, platinum, iridium, titanium, tantalum, or alloys. Such materials are highly visible by fluoroscopy even at very minimal thicknesses.

The security rings 144 and 146 may be attached to the stent 140 by any suitable attachment mechanism to ensure that the security rings 144 and 146 remain in place on the ends of the stent graft. This includes, but is not limited to, suture attachment methods, e.g. where a suture going around one or more struts of the stent is attached to a security ring. Apart from suturing techniques, methods including adhesives also may be used. One can solder or braze the stent and security ring together. Preferably, the security rings 144 and 146 are welded to stent 140 at one or more weld points 152, 153, 154. One advantage of welding the security rings to the stent is to improve the mechanical integrity of the stent graft system. The welding connections may be created by welding techniques using welding technologies such as tungsten inert gas (tig) welds, metal inert gas (mig) welds, laser welds, friction welds, and electron beam welds. Other materials known to accelerate the welding process and improve the strength between the welded elements can be added. Electropolishing may be used to remove processing impurities and form a smooth surface following attachment of the stent to the security rings.

In one embodiment, the stent graft is positioned in a vessel of a patient and the ends of the stent graft are opened first, and then the middle of the stent graft is opened. This method maximizes the ability of the stent graft to capture potential debris material from an underlying stenosis in the vessel. With reference to FIGS. 10 and 11, the hinge points 201, 202, 203 and 204 of end belt 170 are narrower than the hinge points 210, 211, and 212 of belt 162. This feature provides the advantage of requiring less force to open the end belts 170 and 172 than belts 162.

The stent design and functionality in the embodiments described above is not limited to a balloon-expandable stent, but may be employed with the so-called self-expanding stents that are formed for example from shape memory materials such as Nitinol.

From the foregoing it can be seen that there has been provided a stent graft assembly and method which makes it possible to ensure that the graft is maintained in the desired position on the stent at all times and particularly during deployment of the stent graft while readily accommodating expansion of the stent graft after the stent graft has been deployed into the desired position. It also can be seen that use of the security rings serves to prevent inadvertent movement of the graft with respect to the stent or separation of the graft from the stent.

It is claimed:

1. A method of retaining a polymeric sleeve on a stent, where the polymeric sleeve is located over the stent, the stent including an eyelet, the improvement comprising:

engaging the polymeric sleeve with the stent, the sleeve indented within the eyelet by a member frictionally engaged with the sleeve such that the member can be released from a delivery device while engaged with the sleeve, at least a portion of the member being aligned with the eyelet and having a profile that is the same as the profile of the eyelet, and wherein the member does not cross through the sleeve.

2. The method of claim 1, the member comprising a radiopaque marker.

3. The method of claim 2, wherein a plurality of eyelets are included in the stent, each eyelet receiving a radiopaque marker engaging the polymeric sleeve.

4. The method of claim 2, wherein the marker consists essentially of metal.

5. The method of claim 4, wherein the metal is selected from gold, platinum, iridium and tantalum.

6. The method of claim 1, wherein the profile of said at least a portion of the member is circular.

7. The method of claim 1, wherein the profile of said at least a portion of the member is circular.

8. The method of claim 1, wherein the stent is expandable without altering the profile of the eyelet.

9. A stent graft for positioning within a body lumen, the graft comprising a polymeric sleeve and the stent including an eyelet, the improvement comprising:

a member that is frictionally engaged with the polymeric sleeve and that is releasable with the stent graft from a delivery device, the sleeve indented within the eyelet by at least a portion of the member, wherein said at least a portion of the member is aligned with the eyelet and has a profile that is the same as the profile of the eyelet, and wherein the member does not cross through the sleeve.

10. The stent graft of claim 9, the member comprising a radiopaque marker.

11. The stent graft of claim 10, wherein a plurality of eyelets are included in the stent, each eyelet receiving a radiopaque marker engaging the polymeric sleeve.

12. The stent graft of claim 10, wherein the marker consists essentially of metal.

13. The stent graft of claim 12, wherein the metal selected from gold, platinum, iridium and tantalum.

14. The stent graft of claim 9, wherein said at least a portion of the member has a profile that is the same as the profile of the eyelet.

15. The method of claim 14, wherein the profile of said at least a portion of the member is circular.

16. The method of claim 9, wherein the profile of said at least a portion of the member is circular.

17. The method of claim 9, wherein the stent is expandable without altering the profile of the eyelet.

* * * * *